United States Patent [19]

Benfey et al.

[11] Patent Number: 5,110,732
[45] Date of Patent: May 5, 1992

[54] SELECTIVE GENE EXPRESSION IN PLANTS

[75] Inventors: Philip N. Benfey, New York; Nam-Hai Chua, Scarsdale, both of N.Y.

[73] Assignee: The Rockefeller University, New York, N.Y.

[21] Appl. No.: 323,525

[22] Filed: Mar. 14, 1989

[51] Int. Cl.$^5$ .................... C21N 15/79; C07H 15/12; A01H 5/00
[52] U.S. Cl. .................... 435/172.3; 435/240.4; 435/317.1; 435/320.1; 536/27; 800/205; 935/25; 935/30; 935/35
[58] Field of Search ............... 435/172.3, 320, 317.1, 435/240.4; 800/1; 935/30, 25, 35; 536/27

[56] References Cited

PUBLICATIONS

Kay et al., 1987 Science 236: 1299–1302.
Sanders et al., 1987 Nucl. Acids Res. 15:1543–1558.
Poulsen et al., 1988 (Sep.) Mol Gen Genet 214:16–23.
Odill et al., 1985 Nature 313:810–812.

*Primary Examiner*—Elizabeth C. Weimar
*Assistant Examiner*—P. R. Rhodes
*Attorney, Agent, or Firm*—Dennis R. Hoerner, Jr.; Howard C. Stanley

[57] ABSTRACT

Fragments of the 35S promoter of cauliflower mosaic virus are disclosed which exhibit selective expression of chimeric plant genes in plant tissue. Promoter fragment A exhibits selective expression in root tissue and the radical of the seed. Promoter fragment B exhibits constitutive expression in plant tissue other than root tissue.

5 Claims, 3 Drawing Sheets

```
-343
 |
5'-TGAGACTTTT CAACAAAGGG TAATATCCGG AAACCTCCTC

GGATTCCATT GCCCAGCTAT CTGTCACTTT ATTGTGAAGA TAGTGGAAAA

GGAAGGTGGC TCCTACAAAT GCCATCATTG CGATAAAGGA AAGGCCATCG

TTGAAGATGC CTCTGCCGAC AGTGGTCCCA AAGATGGACC CCCACCCCAC

GAGGAGCATC GTGGAAAAAG AAGACGTTCC AACCACGTCT TCAAAGCAAG
                -90
                 |
TGGATTGATG TGAT ATCTCC ACTGACGTAA GGGATGACGC ACAATCCCAC

TATCCTTCGC AAGACCCTTC CTCTATATAA GGAAGTTCAT TTCATTTGGA
                +8
                 |
GAGGACACGC TG-3'
```

FIGURE 1

SELECTIVE GENE EXPRESSION IN PLANTS

BACKGROUND OF THE INVENTION

The present invention relates to plant genetic engineering and more particularly to selective gene expression in plants. The cauliflower mosaic virus (CaMV) 35S promoter has been shown to be highly active in most plant organs and during most stages of development when integrated into the genome of transgenic plants (Odell et al., 1985; Nagy et al., 1985; Jensen et al., 1986; Kay et al., 1987; Jefferson et al., 1987; Sanders et al., 1987). The CaMV 35S promoter can also confer expression in protoplasts of both dicots and monocots (On-Lee et al., 1985; Fromm et al., 1985; Ow et al., 1987; Nagata et al., 1987; Odell et al., 1988). However, it is not strictly an unbiased constitutive promoter. When expression was analyzed in floral tissue by histochemical localization, differences in expression levels between adjacent cells were observed. Differences have also been observed in the expression pattern of the same CaMV 35S promoter construct in independent transgenic plants and in different plant species. These observations suggest that the 35S promoter may contain several cis-elements which differentially interact with trans factors responsible for expression in different cell types.

It is therefore an object of the present invention to provide modified plant promoters which are useful to cause selective expression of chimeric plant genes in plant tissues.

It is therefore another object of the present invention to provide modified CaMV 35S promoters which are useful to cause selective expression of chimeric plant genes in plant tissues.

These and other objects and advantages of the present invention will become apparent from the following description and exemplary embodiments.

BRIEF DESCRIPTION OF THE DRAWINGS

FIG. 1 represents the nucleotide sequence (−343 to +8) for the CaMV 35S promoter.

STATEMENT OF THE INVENTION

Figure 2:
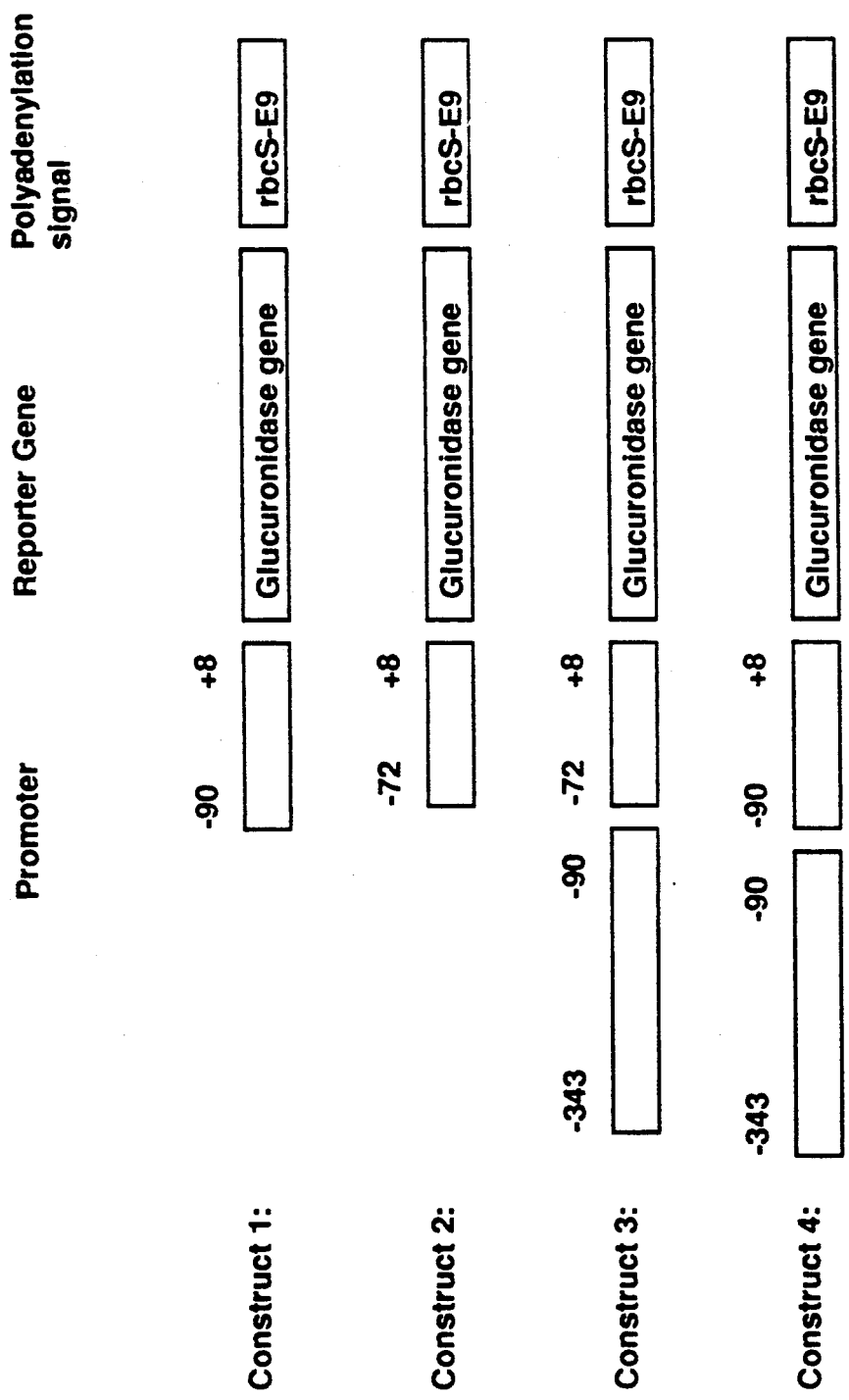
FIG. 2 represents the construction of Construct 1, Construct 2, Construct 3 and Construct 4.

The present invention involves the use of modified CaMV 35S promoters to cause selective expression of plant genes in particular plant tissues.

In one embodiment it was found that the expression conferred by promoter fragment A (nucleotides −90 to +8 of CaMV 35S, FIG. 1) was particularly strong in root tissue and the radical of the seed (a tissue destined to become root). In another embodiment, promoter fragment B (nucleotides −343 to −90 of CaMV 35S, FIG. 1) was strongest in the cotyledons of seeds and seedlings, and the vascular tissue of the hypocotyl. Lower levels of expression were detectable in most other tissues of the seedling, with lowest levels found in non-vascular tissue of the root. It appears therefore that expression conferred by promoter fragment B is detectable in nearly all cell types, but is lowest in those cell types in which expression is highest for promoter fragment A.

Plant Gene Construction

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA. Transcription of DNA into mRNA is regulated by a region of DNA usually referred to as the "promoter." The promoter region contains a sequence of bases that signals RNA polymerase to associate with the DNA and to initiate the transcription of mRNA using one of the DNA strands as a template to make a corresponding strand of RNA.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eukaryotic genes, or from a synthetic gene sequence. In any case, it is preferred that the sequence flanking the initiation site conform to the translational consensus sequence rules for enhanced translation initiation reported by Kozak (1984). The DNA construct of the present invention also contains a structural coding sequence which encodes a protein which is functional in plants. The DNA construct also contains a 3' non-translated region. The 3' non-translated region contains a polyadenylation signal which functions in plants to cause the addition of polyadenylate nucleotides to the 3' end of the viral RNA. Examples of suitable 3' regions are (1) the 3' transcribed, non-translated regions containing the polyadenylation signal of Agrobacterium tumor-inducing (Ti) plasmid genes, such as the nopaline synthase (NOS) gene, and (2) plant genes like the soybean storage protein (7S) genes and the small subunit of the RuBP carboxylase (E9) gene.

Promoter Fragment Constructs

As described above, the CaMV 35S promoter was divided into two fragments promoter fragment A (nucleotides −90 to +8) and promoter fragment B (nucleotides −343 to −90). It was found that these fragments confer markedly different expression patterns in transgenic plants. The expression patterns were defined at the cellular level by histochemical localization. Expression patterns for the two promoter fragments were determined in seeds, seedlings and 7-week old plants.

Figure 3:
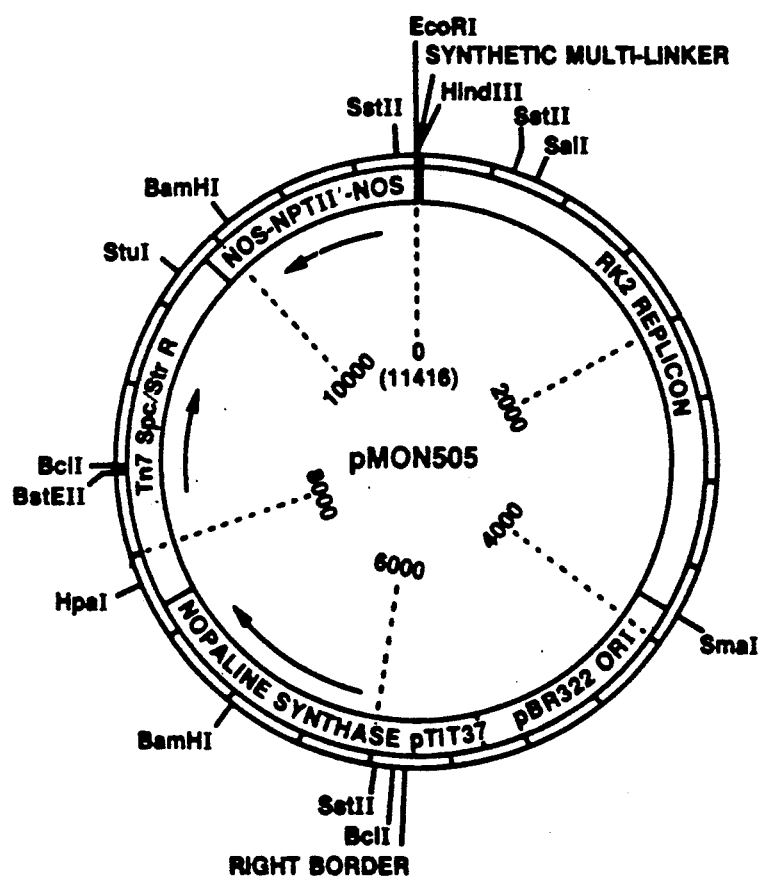
FIG. 3 illustrates a plasmid map of intermediate plant transformation vector pMON505.

The β-glucuronidase (GUS) coding sequence (Jefferson et al., 1987) was used as a reporter gene for the histochemical assay. Referring to FIG. 2, construct 1 was made by cutting a fragment of the 35S promoter deleted to +8 and to which a HindIII linker had been added (as described in Odell et al., 1985) with EcoRV which cuts at −90. The fragment from −90 to +8 was ligated to a fragment containing the β-glucuronidase coding sequence from pRAJ 260 (Jefferson et al., 1987) fused to the pea rbcS 3C 3' end (this fusion product had a HindIII site at the 5' end and an EcoRI site at the 3'end) between the SmaI site and EcoRI site of the polylinker of a derivative of pUC13 which had the HindIII site in the polylinker deleted. The product of this ligation was cut with HindIII, treated with Klenow enzyme and religated in such a way as to destroy the HindIII site. The resulting plasmid was then cut with BamHI and EcoRI and the fragment containing the fusion construct was ligated between the EcoRI and BglII sites of pMON505 (see FIG. 3 and Horsch and Klee, 1986). The entire 35S promoter fragment (−941 to +8) transcriptionally fused to the CAT coding sequence with a pea rbcS-Eg 3' end was then inserted with BglII linkers at the HpaI site of the plasmid.

Preliminary experiments indicated that deletion of promoter fragment A to −72 resulted in complete loss of detectable expression. Therefore, Construct 2 containing the promoter fragment −72 to +8 was used as a negative control. Construct 2 was made essentially in the same manner as Construct 1 except that a 35S fragment from −72 to +8 was fused to the GUS coding sequence as a ClaI (5'), HindIII (3') fragment. The HindIII site was filled in with Klenow enzyme. The ClaI (5'), EcoRI (3') fragment containing the 35S −72 to +8 fragment fused to the GUS coding sequence with a 3' end from the pea rbcS-3C gene was then inserted between the ClaI and EcoRI sites of the polylinker of pMON505 (Horsch and Klee, 1986). A construct containing the 35S promoter (−941 to +8) fused to the Chloramphenicol acetyl transferase (CAT) coding sequence with a 3' end from the pea rbcS-E9 gene was inserted into the HpaI site 4 kilobases (kb) away from the GUS construct. The CAT gene served as a positive indication of plant transformation.

Construct 3 was made by inserting a fragment from the 35S promoter deleted to −343 with attachment of a HindIII linker (as described in Odell et al., 1985) and cut at the EcoRV site at −90 with attachment of a linker that contained an XhoI site, between the HindIII and XhoI sites upstream of the ClaI site in Construct 2.

Construct 4 was made by inserting the same 35S fragment from −343 to '90 between the HindIII and XHoI sites of Construct 1.

Transgenic Plants

The constructs were inserted into intermediate transformation vector pMON505 as described above mobilized into a "disarmed" *Agrobacterium tumefaciens* strain GV3111SE by triparental mating (Rogers et al., 1986). Exconjugants were used to inoculate leaf discs of *Nicotiana tabacum* cv. SRI and regenerated shoots were selected on a medium containing Kanamycin (200 μg/ml) (Rogers et al., 1986). After rooting, transgenic plantlets were transferred to soil and grown in a greenhouse. The primary transformants were allowed to self-fertilize and seeds were collected. For the studies on expression in seedlings and mature plants, seeds were sterilized and germinated on a media containing M.S. salts, 3% sucrose, 0.7% agar, 100 μg/ml Kanamycin, and 500 pg/ml Carbenicillin. The seedlings were maintained at 26° in a cycle of 16 hours light, 8 hours dark. After approximately 21 days two seedlings from each transgenic plant were transferred to Plantcons containing the same media where they continued to grow under the same environmental conditions.

Histochemical Staining

Histochemical staining was performed as described (Jefferson, 1987) with the following modifications. Mature seeds were deposited in a dense monolayer in adhesive (Krazy Glue TM) placed on a section from a carrot. The carrot section was attached to the block used for sectioning supplied with the Vibrotome (TM) sectioning device. Sections of 100 to 200 microns were cut with the Vibrotome and placed directly in the histochemical substrate solution of 1 mM 5-bromo-4-chloro-3-indolyl glucuronide (X-Gluc) and 50 mM Sodium phosphate buffer (pH 7.0) on a microscope slide on which a thin bead of vaseline had been placed around the edge. For some sections the embryos were manually removed from the endosperm with a dissecting needle prior to incubation. The sections were incubated for 12 to 16 hours in a humidified chamber at 37°. Coverslips were placed on the slides before viewing.

Six-day old seedlings were removed from petri dishes, placed directly in the X-Gluc solution and incubated as described above for the seeds. Ten and 17-day old seedlings were removed from petri dishes and placed in a small amount of X-Gluc solution on a microscope slide. The seedlings were then pressed with a second microscope slide. The pressed seedlings were then removed to a fresh microscope slide with X-Gluc solution and incubated as described above for seeds.

For the 7-week old plants, fresh sections were hand cut. Sections from root were placed directly in X-Gluc solution and incubated as described above. Sections from stem and leaf were incubated with the X-Gluc solution in 24-well microtiter dishes for 12-16 hours at 37° C., then cleared of chlorophyll by incubation for ten minutes in a solution of 5% formaldehyde, 5% acetic acid, and 20% ethanol, followed by incubation for two minutes in 50% ethanol, two minutes in 100% ethanol, and two washings in distilled water. The sections were then mounted on microscope slides for photography. Photomicrographs were taken with a Nikon Optiphot microscope using phase contrast optics.

Expression in Mature Seeds

Seeds were harvested from at least eight independent transgenic plants containing each construct. Fresh sections were made by imbedding the seeds in an adhesive and cutting 100 to 200 micron sections. The adhesive acts as a matrix and sections of embryos in all orientations are obtained. These sections were then incubated with the histochemical substrate.

In mature seeds expression from promoter fragment A (Construct 1) was localized to the radical in the embryo and to the endosperm cells at the radical pole. This expression pattern was observed in five of ten plants analyzed, the others showed no detectable expression. Since expression in specific cells of the endosperm was unexpected, the embryo was removed prior to incubation with the substrate to rule out diffusion of enzyme or dye from embryo to endosperm during incubation as the cause of the endosperm staining. Staining was again localized to the radical pole. In contrast, no staining in embryo or endosperm was observed in seeds from 16 independent transgenic plants containing Construct 2 (−72 to +8).

Seeds that contain promoter fragment B (Construct 3) showed expression principally in the cotyledons of the embryo and in the cells adjacent to the cotyledons of the endosperm. This staining pattern was observed in eight transgenic plants. In two others in which staining was quite strong in the cotyledons light staining in the radical was also observed. Expression from the full promoter (A+B, Construct 4) was detected in both the cotyledon and radical of the embryo and in the regions adjacent to the cotyledon and radical of the endosperm in seeds from eight plants.

This data suggests the CaMV 35S promoter can be divided into two functional regions, one from −90 to +8 which is sufficient to confer expression in the radical of the embryo and in the endosperm cells at the radical pole, and the other from −343 to −90 that confers expression in the cotyledons and in the endosperm cells adjacent to the cotyledons. The division is not absolute, when there is high level expression in the cotyledons from the −343 to −90 fragment, there is also low level expression in the radical.

Expression in Seedlings

Seeds were sterilized and germinated on media containing the antibiotics, Kanamycin and Carbenicillin. Since all transformants contain the NPTII (II) coding sequence driven by the nopaline synthetase promoter from pMON505, selection for plants containing the transgene should occur in media that contains Kanamycin.

Seedlings were removed at 6, 10 and 17 days post planting. Tobacco seeds do not germinate synchronously (Avery, 1933), so the developmental stage of all seedlings was not precisely the same. The seedlings were pressed between glass slides in the presence of the histochemical substrate, then incubated with the substrate.

At six days, most seedlings containing promoter fragment A showed no detectable GUS expression. In two of the ten plants analyzed, expression was detected in the root. In seedlings containing promoter fragment B strong staining of the cotyledons was evident, as well as of the stele in the hypocotyl and, in some plants, light staining at the root cap. With the full promoter (fragments A+B) there was strong expression in both root and cotyledons. Seedlings with Construct 2 showed no expression in any tissue.

At ten days, expression from promoter fragment A was detected in eight plants with the strongest staining localized to the root. Staining in the root was most intense at the tip and in root hairs. Seedlings at this stage containing promoter fragment B showed expression restricted to the vascular tissue of the root and in a few plants, some expression at the tip of the root. Plants with the full promoter (fragments A+B) showed expression throughout the root. Plants with Construct 2 showed no expression in the root or in any other tissues.

In the hypocotyl of ten day seedlings containing promoter fragment A, light staining was apparent just below the apical meristem. One plant containing this construct showed light staining in the vascular tissue of the cotyledon. In seedlings containing promoter fragment B, staining was strongest in the vascular tissue of the hypocotyl, and there was no apparent staining just below the apical meristem. In the cotyledons, staining was apparent in the vascular tissue and in mesophyll cells. In seedlings containing the full length promoter (fragments A+B), both vascular tissue and the region just below the apical meristem stained in the hypocotyl.

At 17 days, the expression pattern for seedlings containing promoter fragment A was similar to that at ten days. Intense staining was observed in the root, particularly in lateral roots, even in lateral roots originating in the hypocotyl. Staining in the region just below the apical meristem was also apparent. In seedlings containing promoter fragment B staining in root tissue was still restricted to vascular tissue. However, in the hypocotyl, expression could be detected in cortical and epidermal cells as well as in vascular tissue. In contrast to seedlings with promoter fragment A, lateral roots showed little staining. In the upper hypocotyl more extensive staining was apparent in the region near the apical meristem as well as in the cotyledons and young leaves. For plants containing the full promoter (fragments A+B) strong root expression, as well as expression in most cells of the hypocotyl and of the cotyledons and leaves was observed. Again there was no detectable expression in any tissue of seedlings containing Construct 2. The staining pattern described for promoter fragment B was observed in nine plants. In the tenth plant, more extensive staining was observed in root tissue (cortical cells and root hairs stained) and in the hypocotyl at the 10 and 17 day stage.

These data demonstrate that in seedlings, also, there are two distinct expression patterns conferred by the two promoter fragments. Promoter fragment A appears to confer expression principally in the root tip, and root hairs, and in a region below the apical meristem. Promoter fragment B confers expression in the cotyledons and in the vascular tissue of the hypocotyl and root. The timing of expression seems to differ, also. Expression conferred by promoter fragment A is barely detectable at five days, while expression conferred by promoter fragment B is easily detectable at that stage. The expression pattern when both domains are present in the same construct appears to be the sum of the patterns of the domains alone with some additional staining. This is most apparent in the ten day seedling, particularly in the staining of cortical and epidermal cells of the hypocotyl and root which do not stain with either promoter fragment alone.

Expression at Seven Weeks

The plants were maintained in tissue culture for seven weeks. Fresh sections were cut from younger and older leaves, from upper and lower stems and from roots. To better visualize the histochemical dye, the sections from leaf and stem were stained, then fixed and placed in ethanol to remove chlorophyll.

Plants that contain promoter fragment A showed high expression in the roots. Expression was strongest in the cells at the root tip. Expression was also frequently detected in the cells of the pericycle surrounding the vascular tissue. Staining of cells in the pericycle was observed in regions of the root from which lateral roots were forming. Lower levels of expression were also detected in vascular tissue of younger leaves and in the upper stem. Plants with Construct 2 showed no expression in any tissue.

In plants that contain fragment B at seven weeks expression in the root was detected principally in vascular tissue. In contrast, in the leaf expression was very strong in mesophyll, vascular and epidermal cells. In the stem we observed strong expression in the pith, vascular cells, and cortex. Expression was weaker but still observable in the cortex cells of the leaf midrib, in the epidermal cells of the stem, and in trichomes of both leaf and stem. In plants that contained both fragments A and B, expression in the root was detected in the vascular tissue, pericycle, endodermis and epidermis. In the leaf and stem the expression pattern was indistinguishable from that of fragment B alone.

Variation among Independent Transgenic Plants

Differences in transcriptional regulation conferred by the two promoter fragments were studied in this analysis. Since the RNA species and protein products produced from the four constructs should be identical, the different expression patterns observed are expected to be due to differences in transcriptional activity. However, the use of histochemical localization to detect cell specific expression is not without potential problems. Differences in cell size, metabolic activity, as well as penetration of the substrate into the cell, can contribute to differences in staining intensity. These factors were minimized by use of both positive (Construct 4) and negative controls (Construct 2) and by analysis of at least eight independent transgenic plants for each construct. Variation in the degree of staining among the plants containing Constructs 1, 3 and 4 (Construct 2 was always without staining in all tissues) were observed. For Construct 3, nine of the ten plants analyzed showed the staining pattern described above, but with varying degrees of intensity in the tissues described. One plant containing promoter fragment B showed more extensive expression in the root than did the other nine plants analyzed. There was also one plant containing promoter fragment A that showed more extensive expression in the cotyledon during seedling development. In both cases expression was also particularly strong in the tissues where these domains normally express. The possible reasons for variation among independent transgenic plants are several. Differences in copy number of the transgene and in allele number (heterozygote vs. homozygote) can contribute to variation. Also, the site of integration of the transgene in the chromosome has been cited frequently as a probable cause of quantitative variation in expression (Odell et al., 1985; Sanders et al., 1987). This "position effect" may be due to insertion near cis-elements (positive or negative) that can influence expression from the transgene. Another possibility is that the interaction between trans-factors and cis-elements of the introduced DNA is influenced by the site of integration.

The histochemical staining pattern of expression from Construct A is strongest at the tip of the root in all developmental stages analyzed. Since the root is continually growing this indicates that the gene is turned off as the cells at the tip divide and differentiate and the GUS enzyme is degraded and diluted out by cell division.

BIBLIOGRAPHY

Avery, G. S., *American J. of Botany* (1933) 20, 309–327.
Barker, S. J., Harada, J. J., and Goldberg, R. B., *Proc. Natl. Acad. Sci. U.S.A.* (1988) 85, 458.
Colot, V., Robert, L. S., Kavanagh, T. A., Bevan, M. W., Thompson, R. D., *EMBO J.* (1987) 6, 3559.
Fang, R. X., Nagy, F., Sivasubramaniam, S. and Chua, N. H., *Plant Cell* (1989) 1.
Fromm, M., Taylor, L. P. and Walbot, B., *Proc. Natl. Acad. Sci. U.S.A.* (1985) 82, 582–5828.
Horsch, R. B. and Klee, H. J., *Proc. Natl. Acad. Sci. U.S.A.* (1986) 83, 4428–4432.
Jefferson, R. A., Kavanagh, T. A., Bevan, M. W., *EMBO J.* (1987) 6, 3901–3907.
Jefferson, R. A., *Plant Mol. Biol. Reporter* (1987) 5, 387.
Jensen, J. S., Marcker, K. A., Otten, L., Schell, J., *Nature* (1986) 321, 669.
Kay, R., Chan, A., Daly, M., and McPherson, J., *Science* (1987) 236, 1299–1302.
Kozak, M., *Nature* (1984) 308:241–246.
Nagata, T., Okada, K., Kawazu, T., and Takebe, I. *Mol. Gen. Genet.* (1987) 207, 242–244.
Nagy, F., Odell, J. T., Morelli, G., Chua, N. H., *Biotechnology in Plant Science: Relevance to Agriculture in the Eighties* Zaitlin, M., Day, P., Hollaender, A., eds. (Academic Press, New York, 1985), pp. 227–236.
Nomiyama, H., Fromental, C., Xiao, J. H., Chambon, P., *Proc. Natl. Acad. Sci. U.S.A.* (1987) 84, 7881.
Odell, J. T., Nagy, F., Chua, N. H., *Nature* (1985) 313, 810.
Odell, J. T., Knowlton, S., Lin, W., and Mauvais, C. J., *Plant Mol. Biol.* (1988) 10, 263–273.
On-Lee, T. M., Turgeon, R., and Wu, R., *Proc. Natl. Acad. Sci. U.S.A.* (1986) 83, 6815–6819.
Ondek, B., Shepard, A., Herr, W., *EMBO J.* (1987), 6, 1017.
Ow, D. W., Jacobs, J. D. and Howell, S. H. *Proc. Natl. Acad. Sci. U.S.A.* (1987) 4870–4874.
Poulsen, C. and Chua, N. H., *Mol. Gen. Genet.* (1988) 214, 16–23.
Rogers, S. G., Horsch, R. B., Fraley, R. T., *Methods Enzymol.* (1986) 118, 627.
Sanders, P. R., Winter, J. A., Barnason, A. R., Rogers, S. G., Fraley, R. T., *Nucleic Acids Res.* (1987) 4, 1543–1558.
Schernthaner, J. P., Matzke, M. A., Matzke, A. J. M., *EMBO J.* (1988) 7, 1249.
Schirm, S., Jiricny, J., Schaffner, W., *Genes Dev.* (1987), 1, 65–74.

We claim:

1. In a method for the expression of a chimeric plant gene, the improvement which comprises the use of a tissue-specific promoter fragment which causes tissue-specific expression in leaves, stems, cotyledons, and vascular tissue of the hypocotyl while causing detectable levels of expression in root vascular tissue when operably coupled directly to a DNA segment corresponding to the −72 to +8 promoter fragment of the Cauliflower Mosaic Virus 35S gene, said tissue-specific promoter fragment having the sequence:

```
5'-TGAGACTTTT  CAACAAGGG   TAATATCCGG
   AAACCTCCTC  GGATTCCATT  GCCCAGCTAT
   CTGTCACTTT  ATTGTGAAGA  TAGTGGAAAA
   GGAAGGTGGC  TCCTACAAAT  GCCATCATTG
   CGATAAAGGA  AAGGCCATCG  TTGAAGATGC
   CTCTGCCGAC  AGTGGTCCCA  AAGATGGACC
   CCCACCCCAC  GAGGAGCATC  GTGGAAAAAG
   AAGACGTTCC  AACCACGTCT  TCAAAGCAAG
   TGGATTGATG  TGATA-3'
```

2. A chimeric plant gene comprising in sequence in the 5' to 3' direction a tissue-specific promoter fragment consisting essentially of the sequence:

```
5'-TGAGACTTTT  CAACAAGGG   TAATATCCGG
   AAACCTCCTC  GGATTCCATT  GCCCAGCTAT
   CTGTCACTTT  ATTGTGAAGA  TAGTGGAAAA
   GGAAGGTGGC  TCCTACAAAT  GCCATCATTG
   CGATAAAGGA  AAGGCCATCG  TTGAAGATGC
   CTCTGCCGAC  AGTGGTCCCA  AAGATGGACC
   CCCACCCCAC  GAGGAGCATC  GTGGAAAAAG
   AAGACGTTCC  AACCACGTCT  TCAAAGCAAG
   TGGATTGATG  TGATA-3',
``` operably coupled directly to the −72 to +8 promoter fragment of the Cauliflower Mosaic Virus 35S gene, said −72 to +8 promoter fragment operably coupled to a structural gene.

3. A transformed plant cell comprising a plant gene of claim 2.

4. A plant comprising transformed plant cells of claim 3.

5. A tissue-specific promoter fragment which functions in plants to cause tissue-specific expression in the leaves, stems, cotyledons and the vascular tissue of the hypocotyl and detachable levels of expression in root vascular tissue operably coupled directly to a DNA segment corresponding to the −72 to +8 promoter fragment of the Cauliflower Mosaic Virus 35S gene, said tissue-specific promoter fragment having the sequence from its 5' to 3' termini:

```
5'-TGAGACTTTT  CAACAAAGGG  TAATATCCGG
   AAACCTCCTC  GGATTCCATT  GCCCAGCTAT
   CTGTCACTTT  ATTGTGAAGA  TAGTGGAAAA
   GGAAGGTGGC  TCCTACAAAT  GCCATCATTG
   CGATAAAGGA  AAGGCCATCG  TTGAAGATGC
   CTCTGCCGAC  AGTGGTCCCA  AAGATGGACC
   CCCACCCCAC  GAGGAGCATC  GTGGAAAAAG
   AAGACGTTCC  AACCACGTCT  TCAAAGCAAG
   TGGATTGATG  TGATA-3'
```

* * * * *